United States Patent
Back et al.

(10) Patent No.: US 11,028,315 B2
(45) Date of Patent: Jun. 8, 2021

(54) ZWITTERIONIC SURFACTANTS SUITABLE FOR ENHANCED OIL RECOVERY

(71) Applicant: RHODIA OPERATIONS, Paris (FR)

(72) Inventors: Olivier Back, Lyons (FR); Philippe Marion, Vernaison (FR); Mikel Morvan, Pessac (FR)

(73) Assignee: RHODIA OPERATIONS, Paris (FR)

( * ) Notice: Subject to any disclaimer, the term of this patent is extended or adjusted under 35 U.S.C. 154(b) by 0 days.

(21) Appl. No.: 16/091,227

(22) PCT Filed: Mar. 30, 2017

(86) PCT No.: PCT/EP2017/057493
§ 371 (c)(1),
(2) Date: Oct. 4, 2018

(87) PCT Pub. No.: WO2017/174424
PCT Pub. Date: Oct. 12, 2017

(65) Prior Publication Data
US 2019/0153298 A1    May 23, 2019

(30) Foreign Application Priority Data

Apr. 8, 2016 (EP) .................................. 16305409

(51) Int. Cl.
*C09K 8/584* (2006.01)
*C07C 229/12* (2006.01)
*C07C 309/14* (2006.01)
*E21B 43/16* (2006.01)

(52) U.S. Cl.
CPC ............ *C09K 8/584* (2013.01); *C07C 229/12* (2013.01); *C07C 309/14* (2013.01); *E21B 43/16* (2013.01)

(58) Field of Classification Search
None
See application file for complete search history.

(56) References Cited

U.S. PATENT DOCUMENTS

| | | | | |
|---|---|---|---|---|
| 5,258,137 A * | 11/1993 | Bonekamp | ........... | A62D 1/0071 516/11 |
| 5,607,678 A * | 3/1997 | Moore | ........... | A61K 8/042 424/401 |
| 5,979,557 A * | 11/1999 | Card | ........... | C09K 8/68 166/300 |
| 6,302,209 B1 | 10/2001 | Thompson, Sr. et al. | | |
| 6,435,277 B1 * | 8/2002 | Qu | ........... | C09K 8/68 166/281 |
| 6,703,352 B2 * | 3/2004 | Dahayanake | ........... | C05G 5/20 507/241 |
| 2005/0233911 A1 * | 10/2005 | Samuel | ........... | C09K 8/64 507/238 |
| 2006/0084579 A1 * | 4/2006 | Berger | ........... | C09K 8/12 507/129 |
| 2008/0093073 A1 * | 4/2008 | Bustos | ........... | E21B 43/261 166/279 |
| 2009/0275490 A1 * | 11/2009 | Milne | ........... | C09K 8/68 507/244 |
| 2009/0305914 A1 * | 12/2009 | Li | ........... | C09K 8/64 507/265 |
| 2019/0292131 A1 * | 9/2019 | Back | ........... | C07C 29/145 |

FOREIGN PATENT DOCUMENTS

| | | |
|---|---|---|
| CN | 104109518 A | 10/2014 |
| CN | 104277807 A | 1/2015 |
| WO | 0129369 A1 | 4/2001 |
| WO | 2011038745 A1 | 4/2011 |

\* cited by examiner

*Primary Examiner* — John J Figueroa
(74) *Attorney, Agent, or Firm* — Osha Bergman Watanabe & Burton LLP

(57) ABSTRACT

The instant invention relates to surfactants having the following formula (I) wherein: each of $R^a$ and $R^b$ is a linear or branched, saturated or unsaturated, hydrocarbon chain, each of $R^c$ and $R^d$ is a alkyl chain having 1 to 10 carbon atoms, each of ($E^1$) and ($E^2$) is a divalent hydrocarbon radical, A is: a group a carboxylate group —COO⁻ (optionally in all or part in the form —COOH); or a sulfonate group —SO₃⁻ (optionally in all or part in the form —SO₃H). The invention also relate to the preparation of these surfactants and their use in oil extraction, especially in EOR applications.

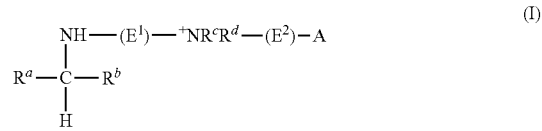

(I)

19 Claims, No Drawings

ZWITTERIONIC SURFACTANTS SUITABLE FOR ENHANCED OIL RECOVERY

This application is a U.S. national phase entry under 35 U.S.C. § 371 of International Application No. PCT/EP2017/057493, filed on Mar. 30, 2017, which claims priority to European application No. 16305409.1, filed on Apr. 8, 2016. The entire contents of these applications are explicitly incorporated herein by this reference.

The present invention relates to zwitterionic surfactants bearing a (sulfo)betaine group that are, inter alia, suitable for enhanced oil recovery (EOR). The invention more specifically relates to specific zwitterionic surfactants, preparation thereof and use in oil recovery from natural oil reservoirs, especially for EOR applications.

In the present description, the generic term "(sulfo)betaine group" refers to a group selected from:
 "betaine" groups, which are defined in the instant decryption as groups carrying a quaternary ammonium (said quaternary ammonium being not a protonated amine) and a non adjacent carboxylate group —COO$^-$, optionally in all or part in its protonated form —COOH; and
 "sulfobetaine" groups, also referred as sultaine groups, which are defined in the instant description as groups carrying a quaternary ammonium (said quaternary ammonium being not a protonated amine) and a non adjacent sulfonate group —SO$_3^-$, optionally in all or part in its protonated (sulfonic acid) form —SO$_3$H.

In the instant description, the expression "surfactants bearing a (sulfo)betaine group" intend to encompass any surfactant carrying at least one group betaine and/or sultaine as defined above, and also mixtures of surfactants each of them carrying at least one group betaine and/or sultaine.

Oil recovery from natural oil reservoirs provides the word economy with the necessary fuel and raw materials for a vast number of processes and products.

Generally, three different techniques are used for recovering oil from natural reservoirs.

During primary recovery the natural pressure of the reservoir or gravity drives oil into the well bore, combined with artificial lift techniques such as pumps which bring the oil to the surface. Only about 10% of the oil content of the reservoir are usually produced during primary recovery.

Secondary recovery techniques extend the reservoirs productive life generally by injecting water or gas to displace the oil and drive it to a production wellbore which ultimately results in the recovery of approximately 20 to 40% of the original oil in place.

In view of the fact that much of the easy to produce oil recoverable by primary or secondary recovery has been exploited with leaving on average 60% or more of the original oil remaining in the reservoir, oil producers are interested in enhanced oil recovery techniques which offer the perspective for ultimately exploiting a higher percentage of the original oil content of the oil reservoir. These techniques are summarized in the term Enhanced Oil Recovery (herein referred to as EOR) or tertiary oil recovery.

EOR especially includes methods that is often referred to as "chemical oil recovery" or "chemical EOR" and involves the use of specific chemical compounds or compositions to increase the effectiveness of water floods or the use of detergent-like surfactants to help lower the interfacial tension between the crude oil in the reservoir and the injected brine which often prevents oil droplets from moving through a reservoir.

Whereas in a fresh oil reservoir the oil is present as a continuous phase in the rock formation, this continuous oil phase disintegrates with increasing primary and secondary recovery leaving the oil in discrete droplets which are retained in narrow pores under the effect of high interfacial tension. Overcoming the capillary forces requires either a high pressure or a very considerable reduction in the interfacial tension between water and oil which is targeted through the use of surfactants. The reduction of interfacial tension achievable depends on a variety of different influencing factors such as reservoir temperature, salinity of the reservoir water and composition of the oil itself.

There is an ongoing need in this connection for compositions suitable for enhanced oil recovery which can be fine tuned according to the specific situation in the reservoir in the geological structure as e.g. salinity of the reservoir water, adjustment of interfacial tension and satisfactory solubility in the stream to be injected.

An object of the present invention is to provide zwitterionic surfactants suitable for use in enhanced oil recovery techniques.

To this end, the instant invention proposes specific surfactants, which are obtained via a new process route and that were not known in the prior art to the best knowledge of the inventors.

More precisely, according to a first aspect, one subject-matter of the instant invention is a surfactant of the formula (I):

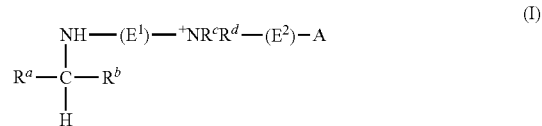

wherein:
 each of $R^a$ and $R^b$, which are identical or different, is a linear or branched, saturated or unsaturated, hydrocarbon chain, that may be interrupted and/or substituted by at least a monocyclic or polycyclic group, that may be, but not necessarily, an aryl group,
 each of $R^a$ and $R^b$ being typically:
  a linear or branched alkyl chain having 1 to 24 carbon atoms, preferably at least 4 carbon atoms (each of $R^a$ and $R^b$ typically carrying from 7 to 17 carbon atoms; it being independently preferred that the sum of the number of carbon in Ra and Rb is of at least 7, preferably of at least 10 and typically of at least 14);
  or a linear or branched alkenyl chain having 1 to 20 carbon, preferably 2 to 20, carbon atoms and having one or more unsaturation (typically 1 to 3);
 each of $R^c$ and $R^d$, which are identical or different, is a linear or branched alkyl chain having 1 to 10 carbon atoms, typically 1 to 4 carbon atoms.
 each of ($E^1$) and ($E^2$) is a divalent hydrocarbon radical, linear or branched, and preferably linear, not substituted or substituted, e.g. carrying a —OH group (especially in $E^2$) and/or optionally carrying a another heteroatom containing group such as an amine, typically an alkanediyl radical of formula —(CH$_2$)$_n$— wherein n=1, 2, 3 or 4 (and wherein at least one of the hydrogen may be substituted by a —OH group, especially in $E^2$, or by an amine)

A is:
a carboxylate group —COO⁻, optionally in all or part in its protonated form —COOH; or
a sulfonate group —SO₃⁻, optionally in all or part in its protonated form —SO₃H (which is generally not the case).

The quaternary ammonium groups of the compounds of formula (I) are associated with counter-anion which may be, in all or part, the group A in an anionic form and/or, in all or part, counter-anions such as chloride, bromide, or sulfate.

Especially for costs reasons, $R^a$ and $R^b$ are preferably linear groups, typically linear hydrocarbon groups. The surfactants of formula (I) possess, as such, a branched structure of their hydrophobic part: $R^a$ and $R^b$ constitute a kind of "twin tail" of the surfactant. The compositions of the invention does not need to make use of branched $R^a$ and $R^b$ groups which are more costly than linear $R^a$ and $R^b$ groups.

According to a first embodiment, the group A is a carboxylate group, optionally protonated in all or part (and preferably partially only). In that case the surfactant of the invention is a betaine of the formula (I-1):

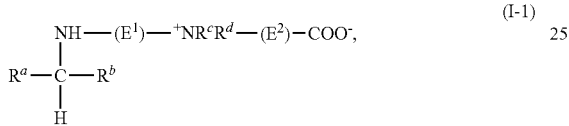

(I-1)

wherein $R^a$, $R^b$, $R^c$, $R^d$, $(E^1)$ and $(E^2)$ have the meaning given herein-above for formula (I). Typically, in the surfactants of formula (I-1), $(E^1)$ is a divalent alkanediyl radical of formula —(CH₂)ₙ— wherein n=1, 2, 3 or 4, preferably 2 or 3 (most typically 3) and $(E^2)$ is a divalent alkanediyl radical of formula —(CH₂)ₙ— wherein n=1, 2 or 3, preferably 1 or 2 (most typically 1);
and wherein:
the amino group —NH— between $(E^1)$ and $CR^aR^b$ may be in its protonated form —NH₂⁺—;
and/or
the COO⁻ group may be in its a protonated form —COOH.

According to a second possible embodiment, the group A is a sulfonate group —SO₃⁻, optionally protonated in all or part (and preferably partially only). In that case the surfactant of the invention is a betaine of the formula (I-2):

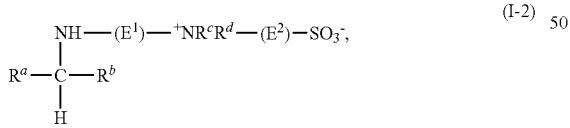

(I-2)

wherein $R^a$, $R^b$, $R^c$, $R^d$, $(E^1)$ and $(E^2)$ have the meaning given herein-above for formula (I). Typically, in the surfactants of formula (I-2), $(E^1)$ is a divalent alkanediyl radical of formula —(CH₂)ₙ— wherein n=1, 2, 3 or 4, preferably 2 or 3 (most typically 3) and $(E^2)$ is a divalent alkanediyl radical of formula —(CH₂)ₙ— wherein n=2, 3 or 4 that may carry an —OH group, typically a —CH2-CHOH—CH2- group;
and wherein:
the amino group —NH— between $(E^1)$ and $CR^aR^b$ may be in its protonated form —NH₂⁺—;
and/or
the SO₃⁻ group may be in its a protonated form —SO₃H.

The invention also relates to mixtures containing at least two distinct surfactants matching the generic definition of formula (I), for example:
at least two distinct surfactants matching the generic definition of formula (I-1) with distinct groups $R^a$ and/or $R^b$; or
at least two distinct surfactants matching the generic definition of formula (I-2) with distinct groups $R^a$ and/or $R^b$.

According to another aspect, the invention relates to a method for preparing the surfactant having the formula (I) as defined herein-above.

This method includes the following steps:
step 1: reacting two acids Ra—COOH and Rb—COOH (the reaction being obtained by reacting a population of acids including these two acids), wherein Ra and Rb are identical or different, via a Piria decarboxylating ketonization, whereby a internal ketone is obtained having the formula (II):

(II)

wherein $R^a$ and $R^b$ have the meaning given herein-above for formula (I)
In this step 1, in practice, the reaction may be conducted on a single fatty acid (in that case Ra=Rb) or on a mixture of distinct acids (whereby a mixture of internal ketone (II) is obtained with a mixture of groups Ra and Rb in the obtained internal ketones).
step 2: reacting the internal ketone (II) obtained in step 1 with a diamine of formula H₂N-(E1)-NR^cR^d in a reductive amination reaction whereby a compound of formula (III) is obtained:

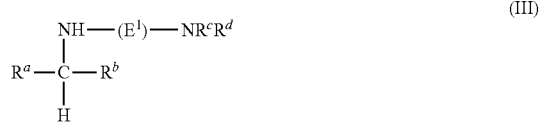

(III)

wherein $R^a$, $R^b$, $R^c$, $R^d$ and $(E^1)$ have the meaning given herein-above for formula (I)
step 3: grafting a group -(E2)-A on the amine group —NR^cR^d of the compound of formula (III) obtained in step (2), wherein $(E^2)$ and A have the meaning given herein-above for formula (I), whereby the compound of formula (I) is obtained.

The surfactants of the invention may be easily prepared from cheap and available (typically naturally occuring) raw materials of relatively low cost, which is a first advantage.

Their three-step preparation process further more allows a good control of their functionalization, which give an access to well defined tailor made molecular structures. By carefully choosing the chain length of the starting fatty acids, it's possible to control the chain length of the fatty ketone and therefore the structure of the final surfactant which allows fine tuning of the properties of the final product.

In addition, according to a specific embodiment, the hydrophobic part of the surfactants of the invention can be entirely saturated, which provides stability against oxidation when compared to unsaturated products.

According to yet another aspect, a subject-matter of the invention is the use of the surfactants of formula (I) for oil recovery, especially for enhanced oil recovery operations.

The inventors have found in the scope of the work which has led to the instant invention that the surfactants of formula (I) have an interesting structure (with a relatively long hydrophobic chain having a polar moiety attached sensibly in the middle (exactly in the middle when $R^a=R^b$, the exact position depending of the nature of $R^a$ and $R^b$). These compounds are of particular interest for EOR application.

More details and preferred embodiments are set forth in the detailed specification hereinafter.

The Zwitterionic Surfactants and their Preparation

The $R^a$ and $R^b$ groups present in the surfactants of formula (I) may be defined by the acids $R^a$COOH and $R^b$COOH from which they are prepared in step 1 as defined hereinabove (and also referred herewith as "fatty acids"), or from which they could have been prepared in the case they are not prepared by making use of this step.

Preferred fatty acids from which the surfactants of formula (I) are actually derived (or theorically derivable) are caprylic acid, capric acid, lauric acid, myristic acid, palmitic acid, stearic acid, naphthenic acids, isostearic acid, arachidic acid, behenic acid, lignoceric acid, cerotic acid or mixtures thereof and preferred acid derivatives are the esters and anhydrides of these acids. Preferred are caprylic acid, capric acid, lauric acid, myristic acid, palmitic acid, stearic acid, naphthenic acids, isostearic acids or mixture thereof.

Other fatty acids from which the surfactants of formula (I) are actually derived (or theorically derivable) comprise one or more double bonds in the chain and include for example oleic acid, linoleic acid, linolenic acid and erucic acid to name only a few examples.

Yet other fatty acids from which the surfactants of formula (I) are actually derived (or theorically derivable) comprise the so called naphthenic acids. The term "naphthenic acid" herein generally denotes a complex mixture of saturated monocarboxylic acids containing cyclopentyl and/or cyclohexyl fragments containing usually 9 to 20 carbon atoms. Naphthenic acids are obtained by oxidation of the naphtha fraction of crude oil and their composition varies with the crude oil composition and the conditions during refining and oxidation.

Preferably, the surfactants of formula (I) are actually prepared from an internal ketone obtained from fatty acids according to step 1 of the process as defined herein-above. In that case, the surfactants of formula (I) may either be obtained from a single fatty acid RaCOOH or from a starting fatty acids mixture. In the case of a mixture of fatty acids, said mixture may be for example a so-called "cut" as typically obtained from vegetable or animal oils through saponification or alcoholysis. More preferably, it may be a fatty acid cut derived from coconut oil or palm kernel oil, that preferably contains a mixture of fatty acids which can comprise fatty acids having 8 carbon atoms up to 18 carbon atoms.

Internal ketones used in step 2 of the process described herein above can alternatively be obtained through cross-ketonization reactions starting from a mixture of linear fatty acids and naphthenic acids, or through cross-ketonization starting from a mixture of aliphatic fatty acids and benzoic acid.

The surfactants of the invention may advantageously been prepared in the following conditions:

Step 1: Decarboxylative Ketonization of Fatty Acids

In this reaction step, fatty acids, preferably saturated straight chain fatty acids, are transformed into the internal ketone (II) through a decarboxylating ketonization reaction. This reaction is typically conducted with the fatty acids in a liquid phase and preferably by continuously removing water formed during the reaction from the reaction mixture.

Step 1 can be applied to a single fatty acid or to a cut of fatty acids generating therefore a cut of fatty ketones of formula (II). Typically the prepared fatty ketones of formula (II) contain the carbonyl group sensibly in the middle of the chain (exactly in the middle when a single fatty acid is used: Ra=Rb, the ketone is symetrical—when starting from a cut of fatty acids, all the possible ketones (II) are formed by combination of the different chains of the starting fatty acids, with a distribution of ketones obtained after the reaction following sensibly a statistical binomial law).

Typically, step 1 may be catalyzed by at least one metal compound, advantageously selected from the group consisting of Mg, Ca, Al, Ga, In, Ge, Sn, Pb, As, Sb, Bi, Cd and transition metals having an atomic number of from 21 to 30 or a mixture thereof or an oxide of these metals or a mixture thereof, preferably in an oxydized state (the metal in its oxidized state may be generated in situ by introducing the corresponding metal at a non oxidized state).

The reaction of step 1 is advantageously catalyzed by compounds of oxydized iron, typically at least one iron oxide, such as magnetite $Fe_3O_4$, and/or $Fe_2O_3$, and/or FeO, the at least one iron oxide being preferably generated in situ in step 1 by introducing metallic iron, typically iron powder (namely: $Fe^{(0)}$) which has the advantage to be a very cheap and abundant material.

When step 1 is carried out in the presence of a metal compound of the type recited above, especially metallic iron, it is advantageous that step 1 comprises two successive stages, namely:

1.1) in a first stage (wherein especially active catalyst species are formed), the metal compound and a first part of the fatty acids (the whole fatty acids being those referred as $R^a$COOH and $R^b$COOH in step 1 of the process) are mixed in a molar ratio of from 1:0.8 to 1:3.5 (molar ratio metal:carboxyl group equivalent) and reacted for a period of from 5 to 300 min at a temperature of from 180 to 270° C., preferably from 190 to 260° C. for a duration of from 5 to 240 min, for example from 15 to 120 min, and preferably in the substantial absence of added solvents, and 1.2) in a second stage, subsequent to stage (1.1), the temperature is raised to 290 to 400° C. and the rest of the fatty acids is added over a period of time of from 1 h to 24 h (typically until the molar ratio of fatty acid to metal is in the range of from 6:1 to 99:1), preferably part by part or continuously. Besides, step 1.2 is preferably conducted in the substantial absence of added solvents After stage (1.2), it can be interesting to separate the metallic compounds from the products (that may be done using conventional techniques) and then to recycle the metallic compounds, e.g. for the conversion of another batch of fatty acids The fatty acids used in the two stages (1.1) and (1.2) preferably comprise at least 10 mol %, based on the entire amount of fatty acids, of fatty acids having 12 carbon atoms or less. Typically, the fatty acids are selected from butanoic acid, hexanoic acid, isostearic acids, caprylic acid, capric acid, lauric acid, myristic acid, palmitic acid, stearic acid, arachidic acid, behenic acid, lignoceric acid, cerotic acid or mixtures thereof, and more preferably the fatty acids comprise 8 to 18 carbon atoms.

Stages 1.1 and 1.2 can also be operated on fatty acid derivatives preferably selected from esters and anhydrides, such as esters or anhydrides of caprylic acid, capric acid, lauric acid, myristic acid, palmitic acid, stearic acid, arachidic acid, behenic acid, lignoceric acid, cerotic acid or mixtures thereof (these derivatives are made preferably from fatty acids containing 8 to 18 carbon atoms).

Step 1 of the process may for example be conducted by:
(a) first reacting, at 220-270° C., typically at about 250° C., metallic iron (e.g. iron powder) with 1.5 to 2.5 equivalents, advantageously 2 equivalents of fatty acids ("first portion" that leads to the formation of iron (II) carboxylate species (with formation of $H_2$), The reaction progress can advantageously be followed by in-situ IR analysis (with lauric acid, for example, which has a large and intense absorption band between 2500 $cm^{-1}$ and 3500 $cm^{-1}$ which is absent in the spectrum of the iron salt);

and then, after a sensibly complete conversion of fatty acids in step a),
(b) the temperature of the reaction mixture obtained by step (a) is risen above 290° C., preferably to about 300° C. (whereby carboxylate salts of iron decompose to iron oxide, fatty ketone and $CO_2$) and maintained at this temperature and the remaining fatty acids are added to the liquid mixture, preferably part by part or continuously.

In step (b), the addition of the fatty acids is advantageously made at a flow, which prevents accumulation of fatty acids in the reaction medium, which can be checked easily using in-situ IR analysis: the fatty ketone (II) displays a $v_{(C=O)}$ absorption which is distinct from the absorption bands of the starting acid and the iron complex). Typically, the rest of the fatty acids introduced in step (b) is added over a period of from 2 to 12 hours.

The ketone (II) acts also as a high boiling point solvent and the water generated during the reaction can therefore be trapped e.g. thanks to a dean-stark apparatus.

At the end of stage (b), the products fatty ketone can be separated from iron compounds, for example as follows:
decantation of solid particles (essentially oxide iron) that are not soluble in the fatty ketone
distillation under reduce pressure (typically 50 mbar, 280-315° C.)
the final mixture can be diluted in $CHCl_3$ and the suspension filtered (typically on a silica plug) and then eluted with $CHCl_3$. Evaporation of the solvent affords fatty ketone free of iron.

Step 2: Reaction of the Ketone (II) with the Diamine (Preparation of Intermediate III)

This step allows a reductive amination of the ketone (II) obtained in step 1.

This reductive amination is preferably performed by reacting the ketone (II) and the diamine of formula $H_2N$-$(E^1)$-$NR^cR^d$ as defined herein-above in the presence of a transition metal (e.g. Ni, Co, Cu, Fe, Pd, Pt) based catalyst (typically Pd/C), under hydrogen pressure (typically between 1 atm. and 200 bar).

According to a possible embodiment, the reaction is carried out in a solvant. However, the presence of such a solvent is not compulsory and according to a specific embodiment, no solvent in used in step 2. The exact nature of the solvent, if any, may be determined by the skilled person. Typical suitable solvents include, without limitation, methanol, ethanol, isopropanol and mixtures thereof.

Besides, Step 2 is usually carried out at a temperature ranging from 15° C. to 300° C.

Step 2 may be conducted batchwise, semi-continuously or continuously and generally performed either in a batch mode or in a continuous mode using a fixed-bed catalyst (gas-solid or gas-liquid-solid process).

A diamine of formula $H_2N$-$(E^1)$-$NR^cR^d$ suitable for step 2 is dimethylaminopropylamine (DMAPA). This amine can be employed in stoichiometric amounts or in excess.

Other example of diamines suitable in step 2 include aminoethylethanolamine (AEEA) and ethylendiamine (FDA).

According to a specific embodiment, the group -$(E^1)$- of the diamine of formula $H_2N$-$(E^1)$-$NR^cR^d$ may comprise an amine group (in that case, the amine may be a triamine: the term "diamine" as used in step 2 intend to encompass compounds including at least two amine group, and optionally more). Examples of amines with more that two amine groups include for example diethylene triamine (DETA), triethylenetetramine (TETA), tetraethylene pentamine (TEPA)

Mixtures of diamines may also be used, including for example mixture of DETA/EDA/AEEA The product (III) of step 2 can be recovered after catalyst separation and removal of solvent and DMAPA excess. Finally the product can be purified, e.g. using standard technics such as distillation.

Step 3: Preparation of the Surfactant from Compound (III)

Grafting the group -$(E^2)$-A on the group —$NR^cR^d$ of the compound of formula (III) obtained in step (2) can be made by the methods described herein or by any technic known by the skilled person.

Surfactant Betaine

For preparing the compound (I-1), step 3 generally comprises a reaction of the compound (III) with a compound of formula X-$(E^2)$-COOH (preferably deprotonated in all or part in the form of a carboxylate) wherein $(E^2)$ is as defined herein-above for formula (I-1) and X is a leaving group, typically an halogen atom such as Cl (Cl is especially suitable) or Br or I, or a sulfonate (optionally substituted for example an alkyl or arylsufonate), a sulfate or a triflate. The compound X-$(E^2)$-COOH may for example be monochloroacetic acid, used in the form of the acetate, for example added as sodium monochloroacetate.

Alternatively, a grafting of a —COOH group may be obtained by reacting the compound (III) with acrylic acid or derivatives thereof.

The reaction may be carried out in a solvant (iPrOH for example). Typically, the reaction is carried out at 25 to 150° C., for example from 50 to 100° C.

Surfactant Sultaine

For preparing the compound (1-2), step 3 may for example comprise a reaction of the compound (III) with a compound of formula X-$(E^2)$-$SO_3H$ (optionally deprotonated in all or part in the form of sulfonate) wherein $(E^2)$ is as defined herein-above for formula (1-2) and X is a leaving group, typically an halogen atom such as Cl (Cl is especially suitable) or Br or I, or a sulfonate (optionally substituted for example an alkyl or arylsufonate), sulfate or triflate. The compound X-$(E^2)$-$SO_3H$ may for example be chlorohydroxypropanesulfonic acid, used in the form of the sulfonate, for example added as sodium chlorohydroxypropanesulfonate. A similar conversion of compound (III) into compound (I) is obtained by reacting the compound (III) together with epichlorhydrin (EPI) and then with sodium bisulfite.

The reaction may carried out in a solvent (iPrOH for example). Typically, the reaction is carried out at 25 to 150° C., for example from 50 to 100° C.

Industrial Applications—EOR

The surfactants according to the invention are of specific interest in EOR applications.

For example, they give rise to low interfacial tension with model alkanes (e.g. dodecane), especially in combination with other hydrophilic surfactants that may improve their solubility in brines applications. One subject-matter of the invention is a method for extracting oil from a subterranean formation, preferably an EOR method, wherein a surfactant of formula (I) is injected in the subterranean formation, preferably in admixture with other hydrophilic surfactants. The invention also relates to the EOR formulations useful in this connection, that comprise at least one surfactant of formula (I), preferably in admixture with other hydrophilic surfactants.

Besides, the surfactants of formula (I) can be used in foam formulations and more particularly low interfacial tension foam formulations once they are mixed with a more hydrophilic anionic surfactant.

One subject-matter of the invention is a method for extracting oil from a subterranean formation, wherein a foam is formed within the subterranean formation, including at least a surfactant of formula (I), preferably mixed with a more additional hydrophilic surfactant.

By way of example of additional surfactants useful with the surfactants of formula (I), one may mention nonionic surfactants, such as alkoxylated nonyl phenol, alkoxylated dinonylphenol, and alkoxylates of various straight and branched alcohols having a carbon chain of preferably from 8 to about 20 or more carbon atoms may be mentioned here. These additional surface active components may also be carboxylated, phosphated, sulfated or sulfonated, i.e. ionized upon use.

The surfactant of the invention may also be use in admixture with other zwitterionic surfactants, (sulfo)betaine surfactants.

A preferred group of additional hydrophilic surfactants which may be used together with the surfactants of formula (I) are alkyl glyceryl ether sulfonates (AGES).

Alkyl glyceryl ether sulfonates (AGES) are well known as detergents utilized in personal care cleansing products and are commercially available from a number of sources. The skilled person will select the best suited AGES based on his professional experience and adapted to the specific case of use so that no further details needs to be given here.

Processes for the manufacture of AGES are described in U.S. Pat. Nos. 3,024,273 and 2,989,547 to which reference is made herewith for further details.

Other surfactants useful in combination with the surfactants of formula (I) are alkoxylated alkyl glyceryl ether sultanates (AAGES) which differ from the alkyl glyceryl ether sulfonates described above by the presence of one or more alkoxy groups between the last carbon atom of the article group and the oxygen atom of the alkyl glyceryl ether sulfonate. AAGES may be represented by the following general formula:

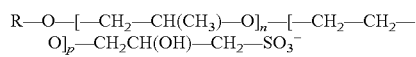

wherein R is a alkyl chain, and n and p are integers of from 0 to 30, preferably of from 2 to 15 and n and p cannot be both equal to 0.

The compositions in accordance with the present invention can contain additional ingredients which are customary ingredients of surfactant flooding compositions for enhanced oil recovery processes.

The way of use of the compositions of the present invention in enhanced oil recovery processing is known to the skilled person and has been described in the literature so that no further details need to be given here. The skilled person will decide on the best process based on his professional experience and taking into account the specific circumstances of the individual application case.

The appended examples illustrate in details preparation of surfactants of the invention and their interest in EOR applications.

EXAMPLES

Example 1

Synthesis of Surfactants of Formula (I)

1.1. Step 1: Synthesis of an Internal Ketone 1.1.1. Synthesis of $C_{23}$-Tricosanone (Internal Ketone from a $C_{12}$ Acid The reaction was carried out under argon in a round bottom flask equipped with mechanical stirring, dean stark apparatus and an addition funnel.

In the reactor, 700 mg of iron powder were dispensed and 20 g of lauric acid was then introduced in the addition funnel. The reaction was conducted as follows:

a first portion of 5 g of lauric acid was added into the reactor and the temperature is brought to 250° C. The mixture is stirred at this temperature for 2 hours during which the color of the media changed to black and $H_2$ gas was released after the stirring of 2 hours, the temperature was risen to 300° C., the mixture was stirred during 1 h30 and then 15 grams of lauric acid were slowly added into the reactor during 4 h30 at a flow which allows keeping concentration of lauric acid in the reaction media very low (no accumulation of free acids in solution).

At the end of the reaction, the addition funnel was replaced by a distillation apparatus and the products were distilled off at 290° C.-340° C. under 50 mbars pressure.

Then the distillation apparatus was again replaced by the addition funnel containing a new amount of 5 g+15 g of fatty acids and the operations described above were repeated for another cycle.

Importantly, no additional amount of iron was introduced. This possible recycling of iron is a generic advantage of step 1: the residue in the flask remaining after distillation is efficient to convert the next batch of acids.

Overall 4 cycles have been carried out without any loss of performances reducing therefore the concentration of iron to less than 1 wt % relative to total fatty acids amount converted.

1.1.2. Synthesis of $C_{15}$-$C_{35}$ Ketones Mixture from a Cut of Fatty Acids ($C_8$-$C_{18}$)

A cut of saturated straight chain fatty acids with a distribution representative of natural coconut oil ($C_8$: 7 wt %, $C_{10}$:

8 wt %, $C_{12}$: 48 wt %, $C_{14}$: 17 wt %, $C_{18}$: 10 wt % and $C_{18}$: 10 wt %) was used in this case.

The reaction was carried out under argon in a round bottom flask equipped with mechanical stirring, dean stark apparatus and an addition funnel.

In the reactor, 3.3 g of iron powder were dispensed and a total 100 g of melted fatty acids were introduced in the addition funnel. The reaction was conducted as follows:

A first portion of 25 g of acid was added into the reactor and the temperature was brought to 250° C. The mixture was stirred at this temperature for 2 hours during which the color of the media changes to black and $H_2$ gas is released.

after the stirring of 2 hours, the temperature was risen to 320° C. and the mixture was stirred during additional 2 h00. The remaining amount of fatty acids (75 grams) is then slowly added into the reactor during 6 h00 at a flow (3 portions of 25 g are added every 2 hours in this case) which allows keeping concentration of free fatty acids in the reaction media very low (no accumulation of free acids in solution). At the end of the addition, the mixture is stirred at 320° C. for an additional 2 h00.

After complete conversion of fatty acids and the intermediate complex, the mixture was then allowed to cool down at room temperature and 200 mL of $CHCl_3$ was added into the reaction vessel.

The suspension was filtered on a silica plug (600 g) and the remaining product was eluted with additional volume of $CHCl_3$. After evaporation of the solvent, 140 g of the sought product (82% isolated yield) was recovered as a white wax.

1.2. Step 2: Synthesis of the Compound (III)

1.2.1. Synthesis from $C_{23}$-Tricosanone (Internal Ketone from a $C_{12}$ Acid)

In a 500 mL round bottom flask equipped with magnetic stirring and condenser are added 10 g (29.56 mmol) of the tricosanone as prepared in example 1.1.1., 120 mL of THF and finally 9.3 mL of DMAPA (73.8 mmol).

The mixture was stirred at room temperature during 1 hour in order to solubilize the ketone and 17.5 mL of $Ti(OiPr)_4$ (59.12 mmol) is added to the reaction mixture which is then stirred at room temperature during 12 hours.

50 mL of MeOH were then added to the mixture followed by the careful addition of 1.7 g of $NaBH_4$ (44.34 mmol). The resulting mixture was then stirred during 4 h00 and 250 mL of $Et_2O$ followed by 250 mL of $H_2O$ are added into the reaction vessel. Upon addition of water a white precipitate of $TiO_2$ was formed which and then removed by filtration.

The organic phase of the filtrate is separated from the aqueous phase and is washed twice with 500 mL of aq. NaOH solution (0.5 M) followed by 500 mL of brine. The organic phase is dried over $MgSO_4$, filtered and evaporated to give a pale yellow oil.

The product is finally purified by flash chromatography on silica gel using $CH_2Cl_2$: MeOH as eluent (from 70:30 to 60:40) to obtain 6 g of the product as a transparent oil. (48% yield).

1.2.2. Synthesis from $C_{15}$-$C_{35}$ Ketones Mixture

The same protocol was applied with the product as prepared in example 1.2.1 starting from the compound as prepared in example 1.1.2

1.3. Step 3: Synthesis of Surfactants

1.3.1. Betaine: Synthesis from the Compound Prepared in Example 1.2.1

In a 50 mL round bottom flask equipped with magnetic stirring and a condenser were successively added 5.57 g of compound prepared in example 1.2.1 (13.12 mmol), 5.5 mL of iPrOH and 6.52 mL of $H_2O$.

1.83 g of sodium monochloroacetate (15.74 mmol) was finally added to the mixture which is stirred at 85° C. during 7 h00. During this time the mixture changes from biphasic to monophasic.

The final betaine solution (35 wt % of active betaine in iPrOH:$H_2O$ 40:60) can be used as such.

NMR analysis of the mixture shows complete conversion of starting diamine and confirms that quaternization takes place exclusively and the tertiary amine moiety of the starting diamine.

1.3.2. Betaine: Synthesis from the Compound Prepared in Example 1.2.2

Same protocol as in 1.3.1 was employed for the synthesis of mixture of betaines from compound prepared in example 1.2.2 The product was obtained in a $H_2O$:iPrOH (60:40) solution (35 wt % active betaine)

1.3.3. Sultaine: Synthesis from the Compound Prepared in Example 1.2.1

In a 50 mL round bottom flask equipped with a mechanical stirring and a condenser 4.18 g of compound prepared in example 1.2.1 (9.84 mmol), 3.4 mL of iPrOH and 4.1 mL of $H_2O$ are added. The mixture is allowed to stir at room temperature and addition of 2.32 g of sodium chlorohydroxypropanesulfonate (11.8 mmol).

The mixture is then stirred at 85° C. during 8 h00. During the course of the reaction, the media changes from biphasic to monophasic.

NMR analysis of the crude shows complete conversion of starting diamine and clean formation of sultaine.

The product is obtained in a $H_2O$:iPrOH (60:40) solution (42 wt % active betaine) and is used as such.

1.3.4. Sultaine: Synthesis from the Compound Prepared in Example 1.2.2

Same protocol as in 1.3.3 was employed for the synthesis of mixture of the compound prepared in example 1.2.2.

Starting from 10 g of ketones, 6 g of pure diamines are obtained after purification (48% yield).

Example 2

EOR Applications of the Surfactants Prepared in Example 1

The surfactants prepared in example 1 (compounds prepared in examples 1.3.1; 1.3.2; 1.3.3; 1.3.4) were mixed with various hydrophilic zwitterionic surfactants.

In contrast to anionic surfactants, betaines of the invention are less sensitive to physicochemical environment changes, i.e. salinity, temperature. Changing the weight ratio between the two zwitterionic surfactants was actually the best way to optimize the formulation and obtain the appropriate phase behavior.

2.1 In the following examples, the performances of surfactants formulations containing the betaine of example 1.3.1 in a brine solution at 50 g/L NaCl were compared.

The total surfactant concentration was set at 8 g/L and the formulation variable was the wt. % of the more hydrophilic zwitterionic surfactant (considered as co-surfactant) in the surfactant blend.

The wt. % of the more hydrophilic zwitterionic leading to a WiII phase behavior (optimal wt %. of co-surfactant), was determined in presence of crude oil at 40° C. and reported in Table 1. The solubility of surfactant blends was also analyzed.

TABLE 1

Performances of surfactants blend. Solubility and Interfacial tension.

| Co-surfactant | Co surfactant Structure | Optimal % co-surfactant | Absorbance | $\gamma_w{}^*$ (mN/m · $10^3$) |
|---|---|---|---|---|
| ADBB12 ** | Branched $C_{12}$ | 71 | 0.45 | 3,4 |
| MackamCET *** | $C_{16}$ | 50 | 0.86 | 2,4 |
| Mackam OB30 *** | $C_{12}$ and $C_{18}$ mixture | 68 | 2 phases | 2,7 |
| Fentapetro BSO *** | $C_{18}$ | 83 | 2 phases | 2,5 |
| Mackam CB-35 *** | Mixture $C_{12}$-$C_{18}$ (coco oil cut) | 40 | 2 phases | 2,5 |

* Calculated as a function of the solubility ratios at the equilibrium phase behavior.
** ADBB12 is an amidopropyl betaine having the formula

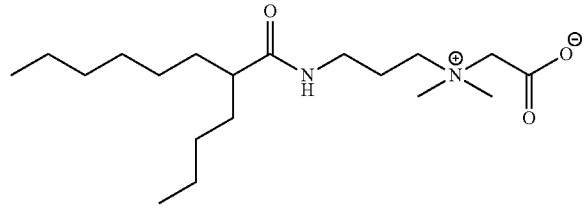 [SMILES: CCCCCCC(CCCC)C(=O)NCCC[N+](C)(C)CC(=O)[O-]]

obtained from 2-butyloctanoic acid (typically $C_{12}$- Guerbet acid e.g. "Isocarb12" from Sasol) through condensation with DMAPA (3-dimethylaminopropyl amine) followed by a reaction with sodium monochloroacetate.
***: available from Solvay company 2.2. In terms of interfacial tension, all the blends studied led to ultra-low values (<$10^{-2}$ mN/m). On the other hand, only the hydrophilic amido betaine derived from a branched $C_{12}$ acid (ADBB12) allows obtaining a homogeneous but opalescent water solution (absorbance of 0.46) at the optimal formulation (71 wt. %).

All the linear alkyl betaines, solutions separate in two phases or forms really turbid solutions (0.86 absorbance). Interfacial tension with crude oil of the mixture ADBB12 and the betaine from $C_{23}$ ketones derived diamine at the optimal wt. % was evaluated by spinning drop methods. The ultra-low interfacial tension was confirmed (=$10^{-3}$ mN/m).

The betaines derived from $C_{15}$-$C_{35}$ ketones mixture have similar behavior than the $C_{23}$ ketones.

Evaluation of the Sultaine Derived from $C_{23}$ Diamine

Sulfobetaine was tested at the same conditions as the betaines obtained from C23 ketone derived diamine. Results are presented in table 2.

TABLE 2

Performances of sulfobetaine from C23 ketone derived diamine blended with ADBB 12

| Co-surfactant | Co surfactant Structure | Optimal % co-surfactant | Absorbance | $\gamma_w{}^*$ (mN/m · $10^3$) |
|---|---|---|---|---|
| ADBB 12** | Branched $C_{12}$ | 64 | 0.84 | 3.3 |

*Calculated as a function of the solubility ratios at the equilibrium phase behavior.
**see Table 1

As the sulfobetaine from C23 ketone derived diamine is more hydrophilic than the betaines form, lower concentration in co-surfactant (ADBB 12) is needed to achieve WiII phase behavior. Furthermore, increasing the concentration of sulfobetaine displace the middle phase microemulsion to a less soluble water region. Same effect is expected using the co-surfactants mentioned in table 1.

Hence betaines from long alkyl chain ketones derived diamine can be used to obtain optimal performances (solubility and interfacial tension) once blended with a more hydrophilic zwitterionic surfactant. Such mixtures can be robust to handle salinity changes in reservoir conditions.

The invention claimed is:

1. A surfactant having the formula (I):

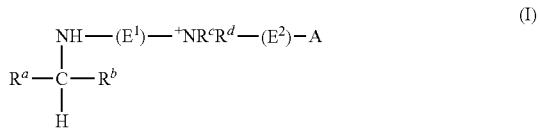

wherein:
each of $R^a$ and $R^b$, which are identical or different, is a linear or branched, saturated or unsaturated, hydrocarbon chain that is optionally interrupted and/or substituted by at least a monocyclic or polycyclic group,
each of $R^c$ and $R^d$, which are identical or different, is a linear or branched, alkyl chain having 1 to 10 carbon atoms,
each of ($E^1$) and ($E^2$) is a divalent hydrocarbon radical linear or branched, not substituted or substituted, optionally carrying a —OH group, and A is:
a carboxylate group —COO⁻, optionally in all or part in its protonated form —COOH; or
a sulfonate group —SO₃⁻, optionally in all or part in its protonated form —SO₃H.

2. The surfactant according to claim 1, which is a betaine of the formula (I-1):

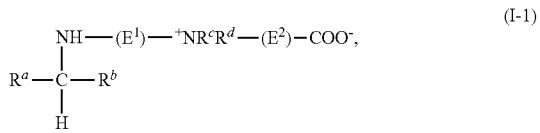

wherein $R^a$, $R^b$, $R^c$, $R^d$, ($E^1$) and ($E^2$) have the meaning given in claim 1 and
wherein:
the amino group —NH— between ($E^1$) and $CR^aR^b$ is in its protonated form —NH₂⁺—; and/or
the COO⁻ group is in its a protonated form —COOH.

3. The surfactant according to claim 1, which is a sultaine of the formula (I-2):

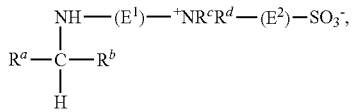
(I-2)

wherein $R^a$, $R^b$, $R^c$, $R^d$, $(E^1)$ and $(E^2)$ have the meaning given in claim 1 and
wherein:
the amino group —NH— between $(E^1)$ and $CR^aR^b$ is in its protonated form —$NH_2^+$—; and/or
the $SO_3^-$ group is in its a protonated form —$SO_3H$.

4. The surfactant according to claim 1, wherein $R^a$ and $R^b$ are linear groups.

5. The surfactant according to claim 4, wherein $R^a$ and $R^b$ are each:
a linear alkyl chain having 1 to 24 carbon atoms; or
a linear alkenyl chain having 1 to 20 carbon atoms and having one or more unsaturations.

6. The surfactant of claim 1, wherein each of $R^c$ and $R^d$, which are identical or different, is a linear or branched, alkyl chain having 1 to 4 carbon atoms.

7. The surfactant of claim 1, wherein each of $(E^1)$ and $(E^2)$ is an alkanediyl radical of formula —$(CH_2)_n$— wherein n=1, 2, 3 or 4, wherein one of the hydrogen may be substituted by a —OH group.

8. The surfactant of claim 1, wherein $(E^2)$ is a divalent hydrocarbon radical linear or branched, not substituted or substituted, carrying a —OH group.

9. The surfactant of claim 1, wherein $(E^2)$ is an alkanediyl radical of formula —$(CH_2)_n$— wherein n=1, 2, 3 or 4, wherein one of the hydrogen is substituted by a —OH group.

10. The surfactant according to claim 9, wherein $R^a$ and $R^b$ are each a linear alkyl chain having at least 4 carbon atoms.

11. The surfactant according to claim 5, wherein the sum of the number of carbon in $R^a$ and $R^b$ is at least 7.

12. An EOR formulation, comprising at least one surfactant of formula (I) according to claim 1 in admixture with other hydrophilic surfactants.

13. A process for preparing the surfactant according to claim 1, the process comprising:
STEP 1: reacting two acids Ra—COOH and Rb—COOH, wherein Ra and Rb are identical or different, via a Piria decarboxylating ketonization, whereby an internal ketone is obtained having the formula (II):

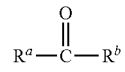
(II)

wherein $R^a$ and $R^b$ have the meaning given in claim 1 for formula (I);
STEP 2: reacting the internal ketone (II) obtained in step 1 with a diamine of formula $H_2N$-(E1)-$NR^cR^d$ in a reductive amination reaction
whereby a compound of formula (III) is obtained:

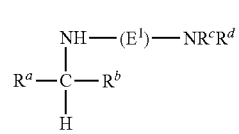
(III)

wherein $R^a$, $R^b$, $R^c$, $R^d$ and $(E^1)$ have the meaning given herein-above for formula (I); and
STEP 3: grafting a group -(E2)-A on the amine group —$NR^cR^d$ of the compound of formula (III) obtained in step (2), wherein $(E^2)$ and A have the meaning given herein-above for formula (I), whereby the compound of formula (I) is obtained.

14. The process of claim 13, wherein step 3 comprises a reaction of the compound (III) with a compound of formula X-$(E^2)$-COOH, optionally deprotonated in all or part in the form of a carboxylate, wherein $(E^2)$ is a divalent hydrocarbon radical linear or branched, not substituted or substituted, optionally carrying a —OH group, and X is a leaving group.

15. The process of claim 14, wherein the compound of formula X-$(E^2)$-COOH is deprotonated in all or part in the form of a carboxylate.

16. The process of claim 14, wherein X is Cl.

17. The process of claim 13, wherein step 3 comprises a reaction of the compound (III) with a compound of formula X-$(E^2)$-$SO_3H$ wherein $(E^2)$ is a divalent hydrocarbon radical linear or branched, not substituted or substituted, optionally carrying a —OH group.

18. A method for extracting oil from a subterranean formation, wherein the surfactant of formula (I) according to claim 1 is injected in the subterranean formation.

19. The method of claim 18, wherein the surfactant of formula (I) is injected in the subterranean formation in admixture with other hydrophilic surfactants.

* * * * *